(12) United States Patent
Avery et al.

(10) Patent No.: US 8,544,815 B2
(45) Date of Patent: Oct. 1, 2013

(54) FLOW CONTROLLER

(75) Inventors: Raymond John Avery, Auckland (NZ); Murray Edward Fenton, Auckland (NZ)

(73) Assignee: Mondiale Technologies Limited, Wellington (NZ)

( * ) Notice: Subject to any disclaimer, the term of this patent is extended or adjusted under 35 U.S.C. 154(b) by 689 days.

(21) Appl. No.: 12/448,464

(22) PCT Filed: Oct. 25, 2007

(86) PCT No.: PCT/NZ2007/000324
§ 371 (c)(1),
(2), (4) Date: Jun. 22, 2009

(87) PCT Pub. No.: WO2008/079023
PCT Pub. Date: Jul. 3, 2008

(65) Prior Publication Data
US 2010/0114041 A1   May 6, 2010

(30) Foreign Application Priority Data

Dec. 22, 2006   (NZ) ......................................... 552376

(51) Int. Cl.
*F16K 7/04* (2006.01)
(52) U.S. Cl.
USPC .................... 251/7; 251/8; 251/208; 251/251; 604/33; 604/34; 604/250
(58) Field of Classification Search
USPC ......... 251/4, 6, 205, 208, 251; 604/248–250, 604/537, 118–119, 32–34
See application file for complete search history.

(56) References Cited

U.S. PATENT DOCUMENTS

| | | | | | |
|---|---|---|---|---|---|
| 1,131,162 | A | * | 3/1915 | Sackett | 81/15.2 |
| 2,010,229 | A | * | 8/1935 | Goff et al. | 251/6 |
| 2,114,139 | A | * | 4/1938 | Crosthwait, Jr. et al. | 251/121 |
| 2,387,660 | A | * | 10/1945 | Hall et al. | 251/9 |
| 2,412,397 | A | * | 12/1946 | Harper | 417/474 |
| 2,582,917 | A | * | 1/1952 | Aagaard | 137/495 |

(Continued)

FOREIGN PATENT DOCUMENTS

| | | |
|---|---|---|
| DE | 3909634 | 9/1990 |
| EP | 0 399 736 | 11/1990 |

(Continued)

OTHER PUBLICATIONS

International Search Report for PCT/NZ2007/000324, mailed Apr. 3, 2008.

(Continued)

*Primary Examiner* — John K Fristoe, Jr.
*Assistant Examiner* — Marina Tietjen
(74) *Attorney, Agent, or Firm* — Nixon & Vanderhye, P.C.

(57) ABSTRACT

A flow controller controls flow through a deformable conduit by compressing the conduit. The conduit may be compressed along a section of its length. The controller may include a cam driven by an actuator, the cam driving a clamp to compress the conduit. The actuator may be a dial. The cam may be shaped such that the flow rate varies linearly with rotation of the dial. The controller may include a clicker to allow the controller to be set in a number of different positions, allowing ease of adjustment and preventing drift or accidental adjustment of the flow rate.

28 Claims, 6 Drawing Sheets

(56) References Cited

U.S. PATENT DOCUMENTS

| | | | | |
|---|---|---|---|---|
| 2,832,560 | A | * | 4/1958 | Grigsby ............................ 251/9 |
| 3,167,085 | A | * | 1/1965 | Redmer .................... 137/315.07 |
| 3,215,394 | A | | 11/1965 | Sherman |
| 3,250,130 | A | * | 5/1966 | Lozano ...................... 73/864.34 |
| 3,289,999 | A | * | 12/1966 | Konzak ............................. 251/6 |
| 3,299,904 | A | * | 1/1967 | Burke ...................... 137/315.07 |
| 3,437,243 | A | | 4/1969 | Farnsworth |
| 3,497,175 | A | | 2/1970 | Koland |
| 3,584,830 | A | * | 6/1971 | Koehn ............................... 251/8 |
| 3,651,831 | A | * | 3/1972 | Gardner ........................ 137/588 |
| 3,756,302 | A | * | 9/1973 | Sivin ............................ 160/23.1 |
| 3,774,876 | A | * | 11/1973 | Melsheimer ...................... 251/8 |
| 3,805,830 | A | | 4/1974 | Smith |
| 3,915,167 | A | | 10/1975 | Waterman |
| 3,984,081 | A | | 10/1976 | Hoganson |
| 4,034,773 | A | | 7/1977 | Huggins |
| 4,071,039 | A | * | 1/1978 | Goof .......................... 137/87.04 |
| 4,272,051 | A | | 6/1981 | Huggins |
| 4,424,832 | A | * | 1/1984 | Koda ............................ 137/844 |
| 4,516,593 | A | * | 5/1985 | Muto ......................... 137/15.14 |
| 4,585,442 | A | | 4/1986 | Mannes |
| 4,660,802 | A | | 4/1987 | Oscarsson |
| 4,697,785 | A | | 10/1987 | Tuseth |
| 5,098,060 | A | * | 3/1992 | Mogler et al. ..................... 251/7 |
| 5,197,708 | A | * | 3/1993 | Campau ............................ 251/8 |
| 5,568,912 | A | | 10/1996 | Minami et al. |
| 5,887,850 | A | * | 3/1999 | Ruffalo ........................... 251/95 |
| 6,036,166 | A | * | 3/2000 | Olson ............................... 251/7 |
| 6,554,589 | B2 | * | 4/2003 | Grapes .................... 417/477.12 |
| 6,589,197 | B1 | | 7/2003 | Doi et al. |
| 6,708,944 | B2 | | 3/2004 | Pfeil et al. |
| 6,862,412 | B2 | | 3/2005 | Kobayashi |
| 6,929,235 | B1 | * | 8/2005 | Height et al. ..................... 251/4 |
| 7,074,212 | B1 | | 7/2006 | Florea |
| 2005/0027237 | A1 | | 2/2005 | Weiner |

FOREIGN PATENT DOCUMENTS

| | | |
|---|---|---|
| EP | 0 482 633 | 4/1992 |
| EP | 0 718 007 | 6/1996 |
| WO | 81/02980 | 10/1981 |

OTHER PUBLICATIONS

Written Opinion of the International Preliminary Examining Authority for PCT/NZ2007/000324, mailed Dec. 9, 2008.

International Preliminary Report on Patentability for PCT/NZ2007/000324, completed Apr. 14, 2009.

* cited by examiner

FLOW CONTROLLER

This application is the U.S. national phase of International Application No. PCT/NZ2007/000324 filed 25 Oct. 2007, which designated the U.S., which in turn claims the benefit of NZ 552376 filed 22 Dec. 2006, the entire contents of each of which are hereby incorporated by reference.

FIELD OF THE INVENTION

The invention relates to fluid flow controllers, in particular controllers which control flow rate by compressing a deformable fluid flow conduit.

BACKGROUND TO THE INVENTION

The administration of medicines, rehydration and nutritional formulations by intravenous (IV) infusion is one of the most common medical procedures employed worldwide. Approximately 2.5 billion IV sets are used annually throughout the world. IV infusion is the fastest way to deliver fluids and medicines throughout the body.

The basic design of the traditional IV flow controller, which has remained unchanged for more than 40 years, is that of a "roller clamp" operated by a thumb wheel. Adjustment of the thumb wheel results in adjustment of the flow rate of the IV solution through compression of an IV drip tubing passing through the device. A typical IV drip set may include a short catheter (needle) for insertion into a vein. The catheter is connected to a length of IV drip tubing, which in turn is connected to a drip chamber inserted into a bag containing the IV drip fluid. The roller clamp is fitted to the IV tubing between the drip chamber and the catheter.

Standard IV drip sets are available in a number of different combinations, including: variable length and diameter of tubing; vents; multi-point injection ports; standard adult IV sets typically having drip chambers with flow rates of 10, 15, 19 or 20 drops per millilitre; standard paediatric IV sets typically having drip chambers with flow rates of 60 drops per ml; and special IV sets with specific, high accuracy drip chambers with flow rates of 60 drops, or more, per ml.

However, the traditional roller clamp exhibits poor accuracy and precision, and is difficult to adjust and operate, making it unsuitable for use by untrained personnel. This inaccuracy is extremely problematic in delivery of therapeutic drug regimes and in the treatment of children, where accurate drug delivery is particularly important. Traditional IV systems also require constant monitoring and adjustment by trained staff, since the flow rate may change over time.

While barely serviceable to the administration of common drug formulations of the 1950s, the roller clamp IV flow controller does not meet the needs of modern clinical treatment regimes. Although various alterations to the standard design have been suggested, none has been entirely successful in solving the problems of this design.

Traditional systems are still widely used in the developing world for all IV clinical applications, including rehydration, drug administration and blood transfusion. However, due to the shortage of trained medical personnel in developing countries, patients are often left to treat themselves or are treated by substantially untrained personnel. Thus, even where developing world patients have access to improved pharmaceuticals and drug treatment regimes, the technology appropriate for delivery of those drugs is generally not available.

The inherent inaccuracy, difficulty of adjustment of conventional IV flow controllers and the reliance on operator calculation of flow rate leads to high incidence of mortality through under-administration of medicines (such as antibiotics, HIV and chemotherapy drugs) and also to increased mortality through inadvertent over-administration of potent chemotherapy and anaesthetic drugs. Thus, patients in developing countries rarely receive the optimum level of clinical care due to over- or under-administration of intravenous medications, often resulting in avoidable fatalities. It is estimated that the over-administration of drugs causes at least 20 million deaths per annum throughout the developing world. This is a "hidden" epidemic because medical staff accept the high mortality rates associated with IV treatments as being normal and when treatment errors occur due to operator error, they are not recorded.

In the developed world, improvements in drug delivery mechanisms have paralleled advances in pharmacology, ensuring safe, accurate and reliable administration of potent drugs. In particular, microprocessor-controlled IV syringe pumps are widely used in the developed world. The higher cost is justified where the cost of medical personnel is high, since these pumps require little monitoring, errors are notified by an audible alarm and drug administration is automatically recorded. However, such drug delivery systems generally cost around US $1500, making them unsuitable for widespread use in poorer countries (although such systems are found in intensive care units in developing countries). Furthermore, the operating costs are relatively high compared to traditional IV systems, and poorer countries generally lack trained support staff for such high-tech equipment. Furthermore, such costly flow controllers are also unsuitable for use in many other cost-sensitive applications. Traditional IV drip systems are also still used in the developed world for certain applications, including hydration therapy, home health care, emergency care etc.

"Dial-a-flow" IV controllers; in which a flow rate can be set using a scale and a dial, are known and provide satisfactory control of flow rates. However, IV fluid passes through the internal parts of such controllers. Therefore, these are disposable, single use devices and are overly expensive for many applications, generally costing about US $5 to $7 per use.

It is an object of the invention to provide a flow controller which provides satisfactory accuracy of flow rate in a cost-effective manner.

It is another object of the invention to provide a flow controller which is reusable, with a long operating life.

It is a further object of the invention to provide a flow controller which is easy to use with minimal training.

It is another object of the invention to provide a flow controller which reduces drift of flow rate over time and prevents accidental adjustment of flow rate.

It is yet another object of the invention to provide a flow controller which will improve the safety and efficacy of IV treatment therapy in the developing world.

Each object is to be read disjunctively with the object of at least providing the public with a useful choice.

SUMMARY OF THE INVENTION

In a first aspect the invention provides a flow controller configured to receive a deformable fluid flow conduit and having:
a clamp having a clamp surface opposing a compression surface and adapted to compress a conduit between the clamp surface and the compression surface, thereby controlling fluid flow through the conduit; and
an actuator allowing adjustment of the clamp;

wherein the clamp surface has a shape which co-operates with the shape of the compression surface so as to compress a conduit substantially uniformly along a section of its length.

In a second aspect the invention provides a flow controller configured to receive a deformable fluid flow conduit and having:

a clamp adapted to compress the conduit, thereby controlling fluid flow through the conduit;

an actuator allowing adjustment of flow rate;

a cam driven by the actuator and configured to adjust the clamp, thereby adjusting the compression of the conduit and the flow rate through the conduit; and a clicker mechanism with a plurality of clicker positions enabling the cam to be fixed in one of a plurality of cam positions, such that the clamp can be set to one of a plurality of settings and retained in that setting.

In a third aspect the invention provides a flow controller configured to receive a deformable fluid flow conduit and having:

a clamp adapted to compress the conduit;

a dial allowing adjustment of flow rate;

a cam driven by the dial and configured to adjust the clamp, thereby adjusting the compression of the conduit and the flow rate through the conduit.

In a fourth aspect the invention provides a flow controller kit including two or more cams, each having a different cross-sectional shape, each cam being configured, when installed in a flow controller, to control flow of a particular fluid and/or administration of a particular treatment regime.

BRIEF DESCRIPTION OF THE DRAWINGS

The invention will now be described by way of example only, with reference to the accompanying drawings, in which.

DETAILED DESCRIPTION

Figure 1:
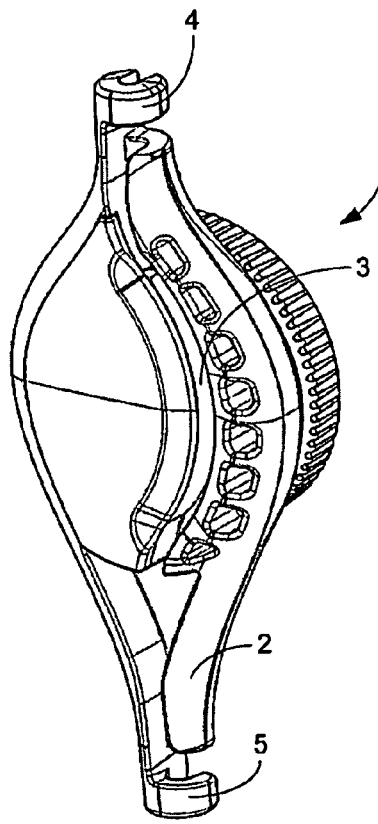
FIG. 1 is a first perspective view of a flow controller according to one embodiment.
Figure 2:
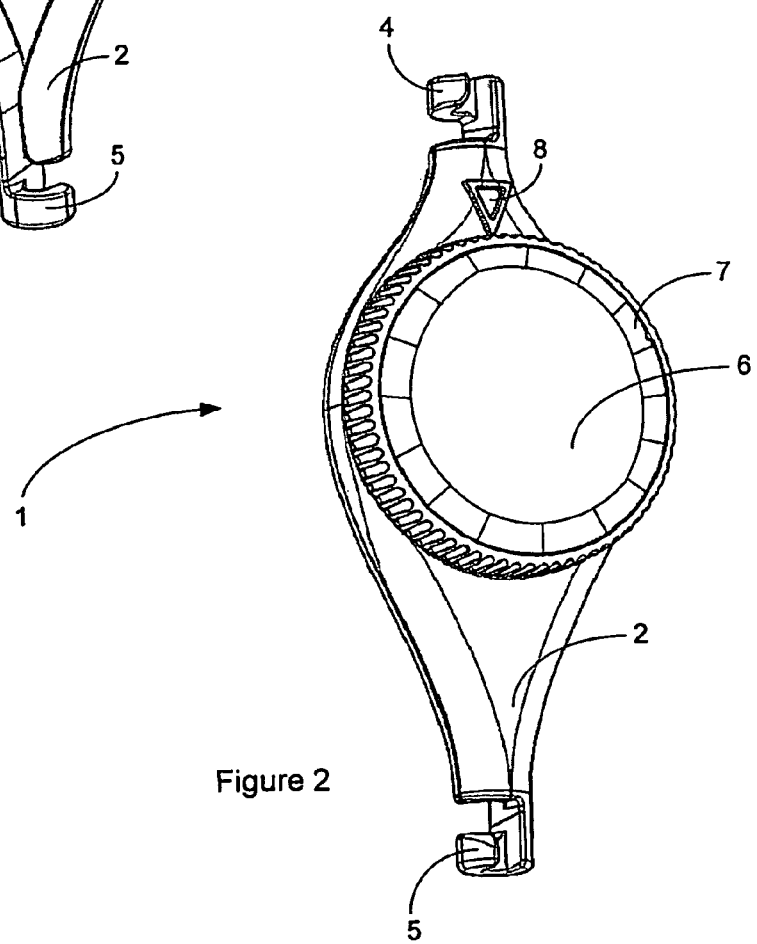
FIG. 2 is a second perspective view of the flow controller of FIG. 1.

FIGS. 1 and 2 show a flow controller 1 having a controller chassis 2 which is adapted to retain a deformable flow conduit in a conduit channel 3. In use, a conduit is inserted into the conduit channel 3 and engages with the retention members 4, 5 at the top and bottom ends of the controller. There is no need to disassemble the flow controller in order to insert the flow conduit.

The flow controller 1 is designed for use with standard IV tubing sets, such as those supplied by Codan or Braun. These suppliers make IV tubing with an outside diameter of about 3.5 to 3.6 mm and a wall thickness of about 0.52 to 0.53 mm. It has been found that the effect of wall thickness on the accuracy and range of the flow controller is much greater than any effect due to tube diameter. IV tubing is also available with a lower wall thickness (for example, one tubing has a wall thickness of about 0.43 mm). While the flow controller described herein has been designed for use with tubings of nominal wall thickness between 0.52 and 0.57 mm, the invention may be applied to tubings of any dimension and wall thickness by suitable design of the components described below (particularly the shape of the cam mechanism).

The flow controller 1 includes an actuator 6, which may be a dial. Alternatively, a sliding actuator, lever or any other suitable actuator may be used. The actuator may be equipped with a scale 7. A pointer 8 may be provided on the controller chassis 2; such that a user can read a value from the scale 7. Of course, the pointer could be provided on the actuator, with a scale on the controller chassis.

The scale may provide an indication of actuator position, or flow rate or any other useful parameter. Different fluids (including IV fluids and drug formulations) have slightly different viscosities and may flow at slightly different rates through a flow conduit. Therefore, the scale may be a scale associated with a particular fluid. The scale could also be associated with a particular drug treatment regime (e.g. a chemotherapy regime) making clinical treatment easier and reducing the possibility of operator error. The scale could be supplied on a sticker suitable for attachment to the flow controller, and the flow controller could be supplied with a number of different stickers suitable for different fluids and/or treatment regimes. Alternatively the sticker could contain a numerical scale which in combination with a reference chart can be used to calculate flow rates in drops per minute and/or millilitres per hour.

Figure 3:
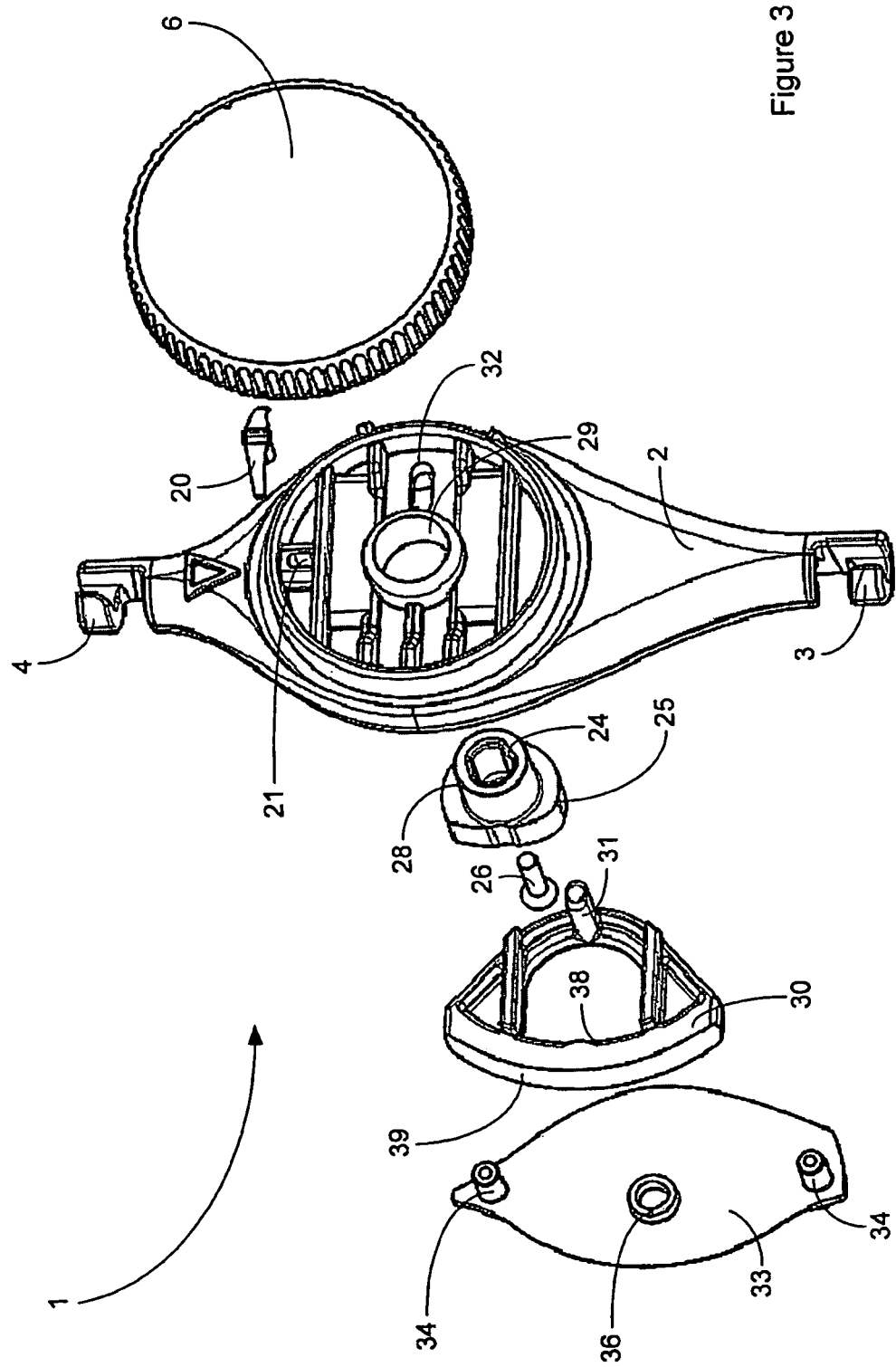
FIG. 3 is a first exploded view of the flow controller of FIG. 1.
Figure 4:
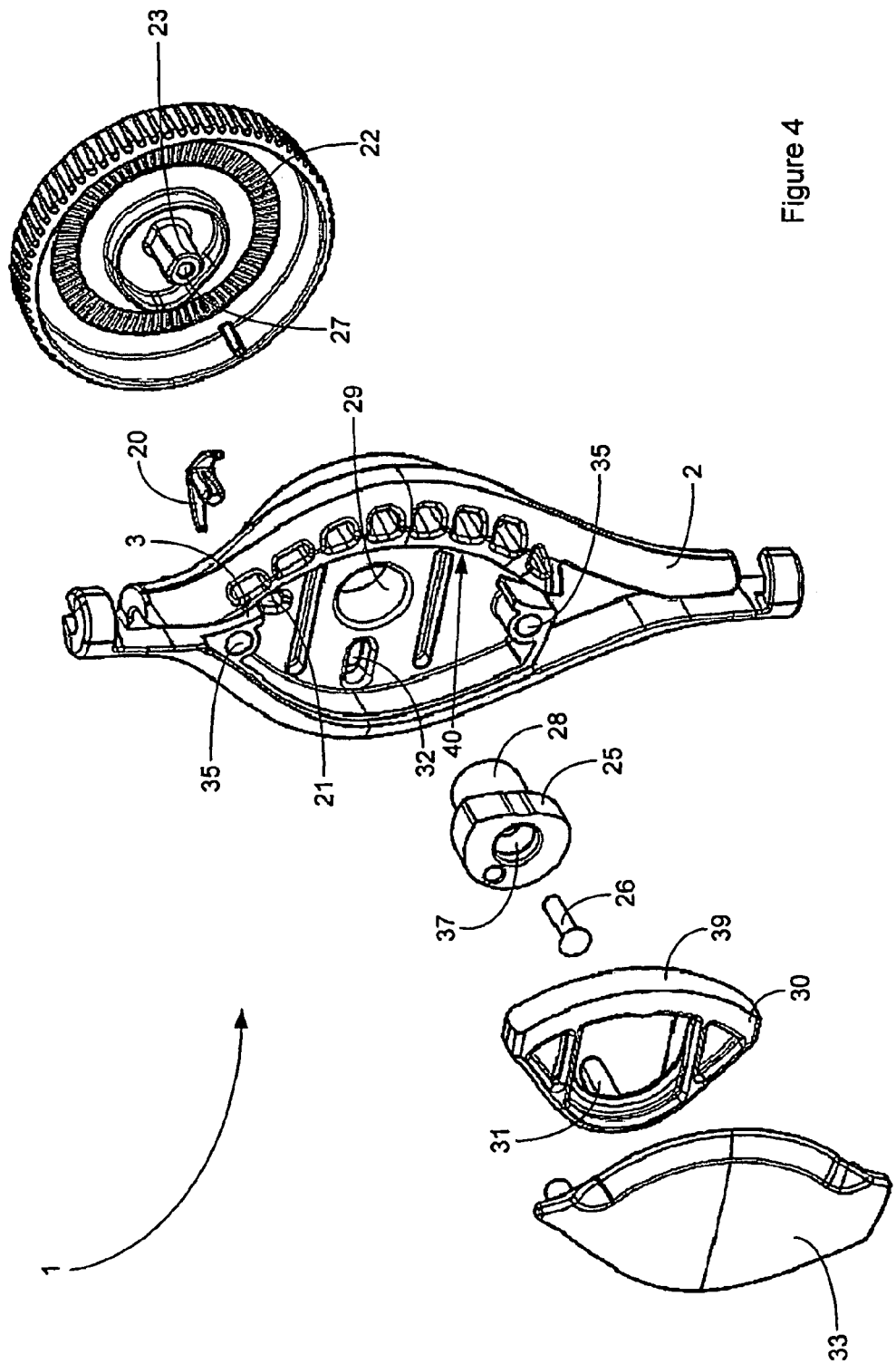
FIG. 4 is a second exploded view of the flow controller of FIG. 1.

FIGS. 3 and 4 show exploded views of the flow controller 1. The flow controller 1 includes a controller chassis 2 (described above), which retains the flow conduit, and also provides a body to which the other elements of the controller are mounted.

The dial 6 mounts to the front surface of the controller chassis 2 and also engages with a clicker 20. The clicker 20 is mounted to the controller chassis in a slot 21 and engages with a series of grooves and projections 22 (FIG. 4) formed on the back face of the dial 6. The clicker mechanism formed by the combination of the clicker 20 and, the grooves and projections 22 allows the position of the dial to be accurately set in one of the positions where the clicker 20 engages with a groove. Furthermore, the projections restrict movement of the dial out of these positions, such that drift of the dial position over time is prevented. This also decreases the chance of the dial setting being accidentally altered by its being knocked etc.

Although the clicker 20 as shown engages with the dial 6, it could also engage with the cam or clamp (both described below). The important feature of the clicker mechanism is that it should operate to allow the clamp (and therefore the flow rate) to be accurately adjusted and to be retained in a particular setting, intermediate a maximum setting and a minimum setting.

The dial also includes a dial shaft 23 (FIG. 4) which engages with the internal bore 24 (FIG. 3) of a cam 25. The dial shaft 23 and the bore 24 may have cooperating non-circular cross-sections. The cam 25 and the dial shaft 23 are secured to each other using a pin 26 which passes through the cam and into a hole 27 provided in the dial shaft 23. The cam is also provided with a cylindrical cam shaft 28 which is seated in a bore 29 in the controller chassis, such that the cam is free to rotate within the bore 29. Thus, the dial and the cam are rotatably secured to the controller chassis, with the dial driving rotation of the cam.

The flow controller 1 also includes a clamp 30. The clamp 30 includes a pin 31 which rides in a slot 32 in the controller chassis 2. The slot 32 is sufficiently long to allow adjustment of the clamp 30 over a desired range. The clamp 30 is secured to the controller chassis 2 by a backing plate 33 having two pins 34 which engage with holes 35 in the controller chassis 2. In addition, the backing plate 33 includes a cylindrical bearing member 36 (FIG. 3) which engages with a hole 37 (FIG. 4) in the back of the cam 25, providing further stability in rotational movement of the cam 25.

The various components may be joined where appropriate using self tapping screws. Alternatively, screws in threaded holes or adhesives or a welding process (such as sonic welding) or simply a friction fit could be used (although this may not last well). However, gluing may be problematic where a number of different materials are used, since a glue is unlikely to bond well to different materials. Sonic welding may suffer from similarly poor bonding where different materials are welded.

When assembled, the cam 25 engages with the inner surface 38 of the clamp 30. When rotated, the eccentric shape of the cam 25 adjusts the lateral position of the clamp 30, and in particular of the clamp surface 39 which, in use, presses against the outside of a flow conduit passing through the flow controller 1. The other side of the flow conduit presses against a compression surface 40 formed by one wall of the conduit channel 3. The clamp surface 39 is shaped with substantially the same profile as the compression surface 40 on the controller chassis 2. When the controller is adjusted to compress a flow conduit, the clamp surface 39 and the compression surface 40 cooperate to provide substantially uniform compression along a section of the conduit's length. The substantially uniform compression and the large operative surface areas of the clamp surface and compression surface provide an increase in flow rate accuracy over prior devices. In contrast, prior devices generally compress a tube at a point, or in a non-uniform manner. This does not allow the flow rate to be adequately controlled.

The large surface areas used in the Applicant's device control flow through interactions of the fluid with the walls of the tube and the size of the flow passage, rather than simply the size of a point constriction. In general, when fluid flows through a tube it flows more quickly at the centre of the tube, and at a minimum speed at the tube walls. The actual flow rate is an average of the flow rate gradient across the cross section of the tube. In the Applicant's device, as the tubing is compressed the effect of the tubing walls on the flow rate increases and the flow rate is slowed. The longer the length of compressed tubing, the greater the effect.

Furthermore, where a point constriction is used, the fluid flow through the constriction is turbulent and satisfactory control of such turbulent flow is difficult to achieve. In contrast, the Applicant's device provides laminar flow through the compressed region, allowing satisfactory control of fluid flow. Again, this laminar flow is achieved through compression of the tubing along a section of its length, rather than at a point.

Therefore, it is desirable to compress the tubing over a section of its length rather than simply at a point. The length of the compressed section may be at least 1 cm, preferably greater than 2.5 cm and more preferably about 5 cm. Similarly, the length of the compressed section may be in the range 1 cm to 10 cm, preferably 2.5 cm to 6 cm and more preferably about 5 cm. The 5 cm length has also been found suitable for ergonomic reasons a device with this length compression fits well in the hand and can be operated one-handed.

The clamp surface 39 and compression surface 40 may be substantially flat surfaces, or may be formed with any suitable pattern of grooves. However, large grooves have been found to cause instability in the change of flow rate with clamp adjustment, while smaller grooves produce approximately the same result as flat surfaces. So, for simplicity of manufacture and best results, flat surfaces are preferred. (The term "flat surface" as used in this specification, including the claims, means a surface free of surface features such as grooves, projections etc. However, a "flat surface" may be a curved surface, such as the clamp surface or the compression surface shown in the drawings.)

Figure 8:
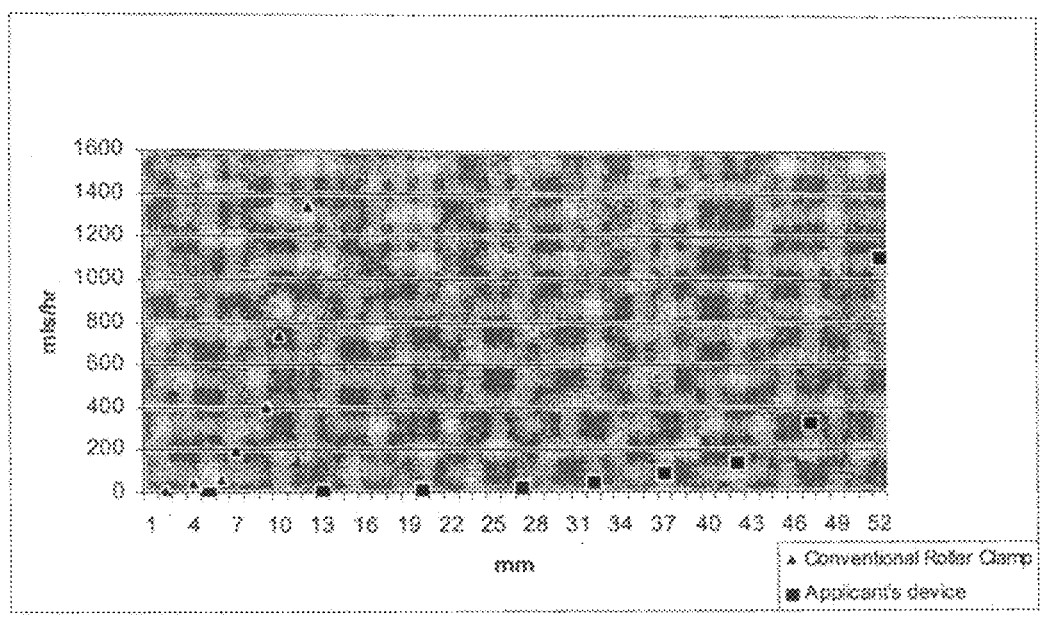
FIG. 8 is a plot showing flow rate as a function of actuator position, for a conventional roller clamp controller and for the Applicant's controller.

An IV tube generally deforms into a FIG. 8 shape between flat plates, forming two channels of flow. It may be possible to use a clamp surface and a compression surface at a slight angle to each other in order to create a single flow channel.

Figure 5:
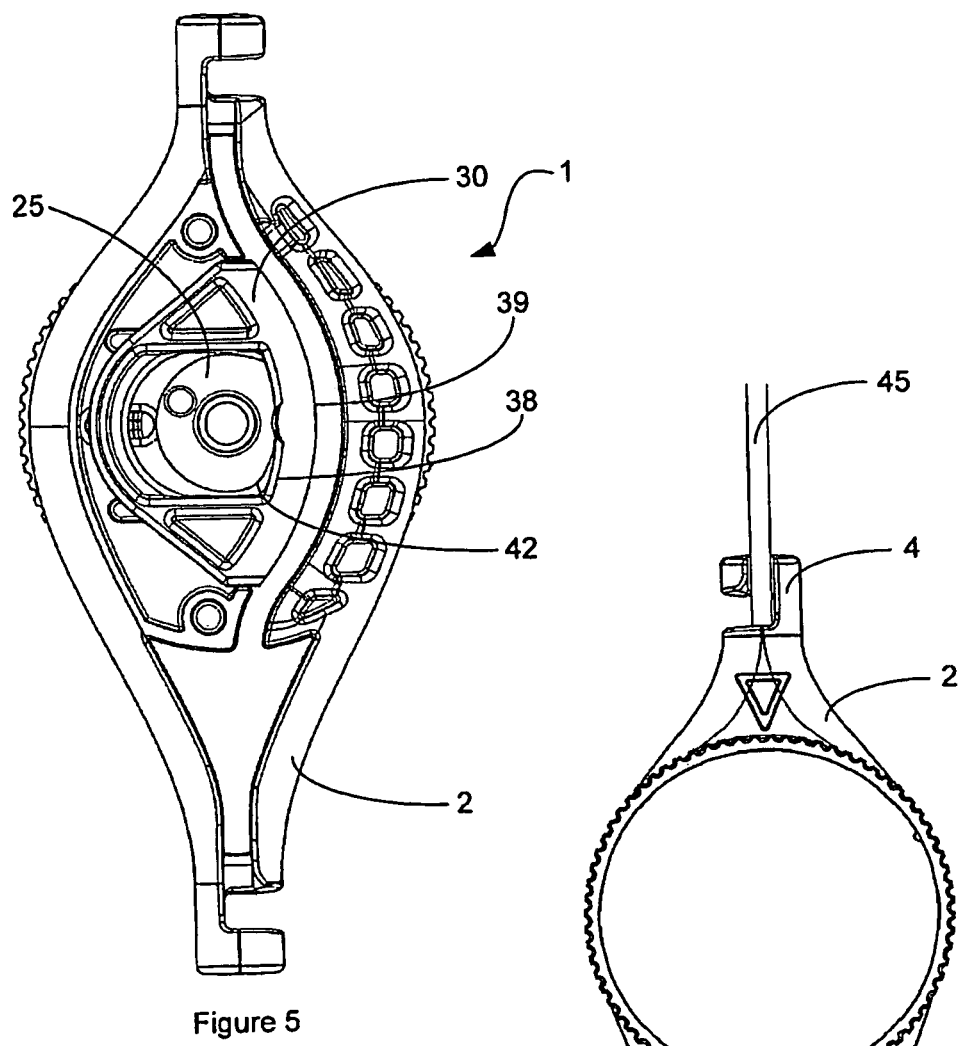
FIG. 5 is a rear view of the flow controller of FIG. 1, before attachment of the backing plate.

The shape of the cam 25 is shown most clearly in FIG. 5, which shows the flow controller 1 from the back, before attachment of the backing plate 33. The operating surface 42 of the cam 25 contacts the inner surface 38 of the clamp 30, driving it laterally when the dial and cam are turned by a user.

The profile of the cam's operating surface 42 may be designed such that the cam radius increase continuously with rotation (where the cam radius is the distance from its axis to the operating surface 42). The profile may be designed to provide a linear or near linear relationship between actuator position and flow rate. Different portions of the profile may have different shapes. For example, the profile may be designed to provide a first rate of adjustment of clamp position with rotation of the cam over a first portion, and a second rate of adjustment of clamp position with rotation of the cam over a second portion. For example, the cam may be designed to provide fine adjustment of clamp position (and therefore flow rate) at low flow rates and slightly coarser adjustment of clamp position at high flow rates. The cam may have a first region covering about 90° of rotation and providing a total increase in cam radius of about 3 mm, allowing the tube to be loaded after it has been fitted to the flow controller. A second region covering about 135° of rotation may provide a total increase in cam radius of about 1 mm; allowing fine adjustment of flow rate. Accurate adjustment of flow rates requires the cam to be fabricated with tight tolerances.

The various components of the flow controller may be formed from plastic materials such that they can be formed by known moulding techniques. Polycarbonate, polysulphone and acetal may be suitable materials. As accuracy is paramount, the low shrinkage of polycarbonate components during fabrication is advantageous, since accurate moulds can be fabricated and the finished part will match the mould closely. However, movement of polycarbonate against polycarbonate creates wear, which will reduce accuracy over time. Therefore, adjacent moving parts should not both be made of polycarbonate. In particular, the dial and the cam should be formed from different materials.

The following combination of materials has been found suitable. The controller chassis 2, dial 6 and back plate 33 are formed from polycarbonate. The clamp 30 may be formed from either polycarbonate or polysulphone. The cam 25 and the clicker 20 are formed from acetal.

Figure 6:
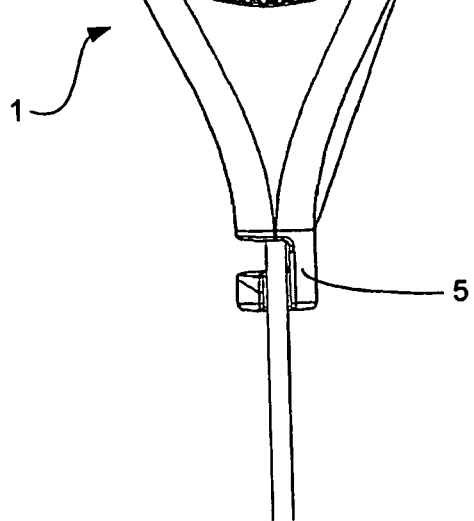
FIG. 6 is a front view of the flow controller of FIG. 1, with a flow conduit in place.
Figure 7:
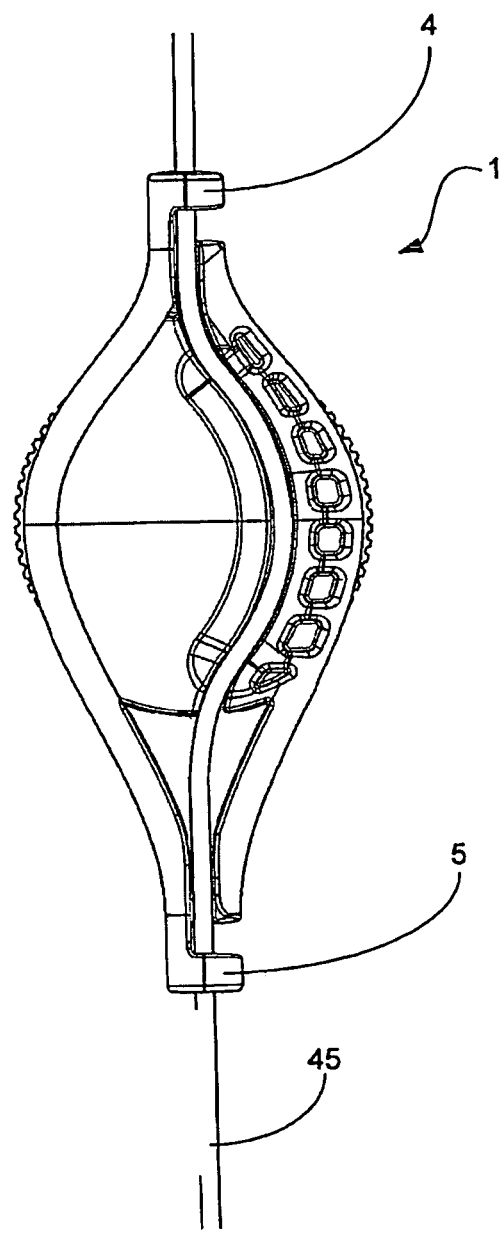
FIG. 7 is a rear view of the flow controller of FIG. 1, with a flow conduit in place.

The flow controller is reusable, clipping onto a deformable flow conduit such as a standard IV tubing 45, as shown in FIGS. 6 and 7. The controller can be easily attached to and removed from the conduit. Fluid never contacts the flow controller, being confined to the inside of the flow conduit. The flow rate can be accurately and simply adjusted. The large compression area formed by the cooperating shapes of the clamp surface 39 and the compression surface 40 provides accurate and precise adjustment of flow rate. The clicker mechanism allows that flow rate to be accurately set and retains the dial, cam and clamp in a set position, preventing creep or accidental adjustment of flow rate. The cam may be shaped to provide substantially linear adjustment of flow rate with rotation of the dial, or may be shaped to provide any other desired relationship between flow rate and dial rotation.

FIG. 8 shows a plot of flow rate as a function of actuator adjustment for a conventional roller clamp controller and for the Applicant's device. The Applicant's device shows more sensitive adjustment and a long substantially linear region between about 0 and 45 mm of adjustment.

The simple operation of this device makes it possible to set flow rate accurately with minimal training. Once the flow rate at a given flow controller setting has been established for a given IV fluid or drug preparation, there is no need for operators to count drops over a period of time in order to set that flow rate; the desired flow rate can simply be set using the dial. The average accuracy of flow rate setting is at a similar level to many state-of-the-art microprocessor controlled IV devices, which currently cost around US$1500.

The controller provides an accurate and simple means of adjusting flow rate at a reasonable cost. The flow controller is expected to cost about the same as existing dial-a-flow controllers. However, while those controllers are single use devices, the Applicant's device is reusable and designed to have an operating life of at least 10 years. This makes the Applicant's flow controller a viable option for use in cost-sensitive applications, including health care in the developing world and other cost-sensitive applications worldwide.

The flow controller has also been found to be less sensitive to variations in flow rate caused by changes in the relative height of an IV drip bag (which may be caused by an actual change in the bag height or a change in height of the patient, or the patient's arm etc). In traditional "roller clamp" flow controller systems the change in pressure caused by changes in bag height may have a marked effect on flow rate.

The flow controller, when used with standard IV tubing has been found suitable for accurate setting of any flow rate between 1 ml/hour to 500 ml/hour. Other suitable flow ranges may be available by altering the tubing used and the parameters of the device, such as length of the clamp and compression surfaces. For example, a flow controller having a flow rate range of 0.5 to 250 ml/hour could be provided.

The invention may be useful in many applications where it is necessary to control fluid flows, including: administration of fluids to human patients, including IV fluids such as rehydration fluids, drug therapy regimes, anaesthetics and palliative care treatments; administration of fluids to animals (i.e. by veterinarians); administration of fluids in a remote setting or by paramedics; and controlling flow of chemicals in various settings, including controlling chemical flow for treatment of water, such as drinking water or sewage.

The flow controller may be provided in kit form. For example, the flow controller may be provided in a kit including a flow controller and two or more stickers each marked with a scale. Each sticker may be marked with a scale suitable for flow control of a particular fluid or administration of a particular treatment regime. In this specification, "particular fluid" includes a particular class of fluids, for example fluids with a viscosity in a particular range. Similarly, the flow controller could be supplied marked with a single scale, but with a conversion chart allowing conversion of the scale reading to a flow rate, or a flow rate for a particular fluid, or two or more different fluids. The flow controller could also be supplied in a kit including two or more cams, each with a different cross-section, so as to provide different relationships between flow rate and actuator position. Each cam could be suitable for flow control of a particular fluid or administration of a particular treatment regime.

While the present invention has been illustrated by the description of the embodiments thereof, and while the embodiments have been described in detail, it is not the intention of the Applicant to restrict or in any way limit the scope of the appended claims to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departure from the spirit or scope of the Applicant's general inventive concept.

The invention claimed is:

1. A flow controller configured to receive a deformable fluid flow conduit and comprising:
   i. a clamp having a clamp surface opposing a compression surface and adapted to compress a conduit between the clamp surface and the compression surface, the clamp being adjustable over a range of clamp positions to control fluid flow through the conduit within an operative range of fluid flow rates;
   ii. an actuator allowing adjustment of the clamp;
   iii. a flow rate scale; and
   iv. a cam driven by the actuator and configured to adjust the clamp:,
   wherein the clamp surface has a shape which co-operates with the shape of the compression surface so as to compress a conduit substantially uniformly along a section of its length between the clamp surface and the compression surface, at all flow rates within the operative range of fluid flow rates, the section of length being at least 2.5 cm in length;
   wherein, the actuator is manually adjustable to set a flow rate to a desired flow rate setting as indicated by the flow rate scale; and
   wherein the clamp surface and the compression surface are opposing substantially flat surfaces widthwise.

2. A flow controller as claimed in claim 1 wherein the clamp surface and compression surface cooperate to compress a conduit along a section of its length such that flow rate is substantially controlled by interactions of fluid with the conduit walls.

3. A flow controller as claimed in claim 1 wherein the clamp surface and compression surface cooperate to compress a conduit along a section of its length such that fluid flow through the compressed conduit is laminar.

4. A flow controller as claimed in claim 1 wherein the clamp surface and compression surface cooperate to compress a conduit along a section of its length which is in the range 2.5 cm to 10 cm in length.

5. A flow controller as claimed in claim 1 wherein the clamp surface and compression surface cooperate to compress a conduit along a section of its length which is in the range 2.5 cm to 6 cm in length.

6. A flow controller as claimed in claim 1 wherein the clamp surface and compression surface cooperate to compress a conduit along a section of its length which is about 5 cm in length.

7. A flow controller as claimed in claim 1 wherein the cam is eccentrically shaped such that flow rate through the conduit varies substantially linearly with movement of the actuator.

8. A flow controller as claimed in claim 1 wherein the cam radius increases continuously with rotation.

9. A flow controller as claimed in claim 1 wherein the cam radius increases at a first rate over a first region and increases at a second rate over a second region.

10. A flow controller as claimed in claim 1 wherein the actuator is a dial.

11. A flow controller as claimed in claim 1 wherein the scale is particular to the viscosity of a particular fluid.

12. A flow controller as claimed in claim 1, further comprising a clicker mechanism with a plurality of clicker positions such that the clamp can be set to one of a plurality of settings and retained in that setting.

13. A flow controller as claimed in claim 1 further comprising a controller chassis providing the compression surface.

14. A flow controller as claimed in claim 1, for controlling delivery of fluids to a human or animal patient.

15. A flow controller configured to receive a deformable fluid flow conduit and comprising:
   i. a clamp having a clamp surface opposing a compression surface and adapted to compress a conduit between the clamp surface and the compression surface, the clamp being adjustable over a range of clamp positions to control fluid flow through the conduit within an operative range of fluid flow rates;
   ii. an actuator allowing adjustment of the clamp;
   iii. a flow rate scale;
   iv. a cam driven by the actuator and configured to adjust the clamp; and
   v. a controller chassis providing the compression surface,
   wherein the clamp surface has a shape which co-operates with the shape of the compression surface so as to compress a conduit substantially uniformly along a section of its length between the clamp surface and the compression surface, at all flow rates within the operative range of fluid flow rates, the section of length being at least 2.5 cm in length;
   wherein, the actuator is manually adjustable to set a flow rate to a desired flow rate setting as indicated by the flow rate scale.

16. A flow controller as claimed in claim 15 wherein the clamp surface and compression surface cooperate to compress a conduit along a section of its length such that flow rate is substantially controlled by interactions of fluid with the conduit walls.

17. A flow controller as claimed in claim 15 wherein the clamp surface and compression surface cooperate to compress a conduit along a section of its length such that fluid flow through the compressed conduit is laminar.

18. A flow controller as claimed in claim 15 wherein the clamp surface and compression surface cooperate to compress a conduit along a section of its length which is in the range 2.5 cm to 10 cm in length.

19. A flow controller as claimed in claim 15 wherein the clamp surface and compression surface cooperate to compress a conduit along a section of its length which is in the range 2.5 cm to 6 cm in length.

20. A flow controller as claimed in claim 15 wherein the clamp surface and compression surface cooperate to compress a conduit along a section of its length which is about 5 cm in length.

21. A flow controller as claimed in claim 15 wherein the cam is eccentrically shaped such that flow rate through the conduit varies substantially linearly with movement of the actuator.

22. A flow controller as claimed in claim 15 wherein the cam radius increases continuously with rotation.

23. A flow controller as claimed in claim 15 wherein the cam radius increases at a first rate over a first region and increases at a second rate over a second region.

24. A flow controller as claimed in claim 15 wherein the actuator is a dial.

25. A flow controller as claimed in claim 15 wherein the scale is particular to the viscosity of a particular fluid.

26. A flow controller as claimed in claim 15, further comprising a clicker mechanism with a plurality of clicker positions such that the clamp can be set to one of a plurality of settings and retained in that setting.

27. A flow controller as claimed in claim 15 wherein the clamp surface and the compression surface are opposing substantially flat surfaces.

28. A flow controller as claimed in claim 15, for controlling delivery of fluids to a human or animal patient.

* * * * *